(12) United States Patent
Rovner (10) Patent No.: US 10,591,327 B2
(45) Date of Patent: Mar. 17, 2020

(54) METHOD AND SYSTEM FOR MEASURING STEAM MASS FLOW

(71) Applicant: Nokomis, Inc., Charleroi, PA (US)

(72) Inventor: Joel B Rovner, West Newton, PA (US)

(73) Assignee: Nokomis, Inc., Charleroi, PA (US)

( * ) Notice: Subject to any disclaimer, the term of this patent is extended or adjusted under 35 U.S.C. 154(b) by 0 days.

(21) Appl. No.: 16/018,424

(22) Filed: Jun. 26, 2018

(65) Prior Publication Data
US 2019/0390988 A1  Dec. 26, 2019

(51) Int. Cl.
| | |
|---|---|
| *G01F 1/66* | (2006.01) |
| *G01F 1/708* | (2006.01) |
| *G01N 21/01* | (2006.01) |
| *G01N 21/17* | (2006.01) |
| *G01F 1/86* | (2006.01) |

(52) U.S. Cl.
CPC ............... *G01F 1/661* (2013.01); *G01F 1/662* (2013.01); *G01F 1/7086* (2013.01); *G01F 1/86* (2013.01); *G01N 21/01* (2013.01); *G01N 21/17* (2013.01); *G01N 2021/1704* (2013.01); *G01N 2021/1736* (2013.01)

(58) Field of Classification Search
CPC .. G01F 1/661; G01F 1/66; G01F 1/86; G01N 21/01; G01N 21/17
USPC ......................................................... 356/437
See application file for complete search history.

(56) References Cited

U.S. PATENT DOCUMENTS 4,480,483 A * 11/1984 McShane ................ G01F 1/661
73/861.27

* cited by examiner

*Primary Examiner* — Roy M Punnoose (57) ABSTRACT

A method and system for measuring steam mass flow in a conduit by simultaneously measuring absorbance and variable steam patterns by light detectors receiving coherent light.

15 Claims, 6 Drawing Sheets

METHOD AND SYSTEM FOR MEASURING STEAM MASS FLOW

FEDERALLY SPONSORED RESEARCH OR DEVELOPMENT

N/A

REFERENCE TO SEQUENCE LISTING, A TABLE, OR A COMPUTER PROGRAM LISTING COMPACT DISC APPENDIX

N/A

BACKGROUND OF INVENTION

To detect steam flow rates, current systems utilize vortex shedding meters, orifice plate flow meters, turbine flow meters, Coriolis mass flow meters, resistance thermometer flow meters, and ultrasonic flow meters, all of which have resulted in a variety of different costs and deficiencies. Some of the problems these flow meters have created include the impedance of the steam flow, the high maintenance costs from moving parts, and low accuracy. Most of these systems require the presence of a physical object in the path of the steam that results in low turndown ratios (the range of flow a flow meter can measure). Additionally, these systems are often susceptible to saturated steam that can condense onto an obtrusion and result in inaccurate mass flow readings. Other problems include their inability to detect sudden fluctuations present in the steam flow rate generated by pressure or temperature variations within these systems.

Laser-based systems generally measure the quality of steam (liquid phase of water as opposed to the vapor phase). Those laser-based systems that attempt to measure mass flow rely on phase change measurements or other more complex methods.

BRIEF SUMMARY OF INVENTION

The technical challenge is the accurate measurement of steam mass flow in a conduit where there is variability in the steam flow. The solution is to simultaneously sample transmitted coherent light with light detectors spaced along the longitudinal axis of the conduit. This arrangement allows for the measurement of parameters that result in a measurement of steam mass flow.

The use of the term steam in this application is for convenience. The method and system applies to any two (2) phase system that is translucent. Two (2) phase is defined by state of matter such as gaseous, liquid and solid and is not limited to mixtures of the same species.

DETAILED DESCRIPTION OF INVENTION

A laser-based approach that will result in a flow meter that will be immune to the problems created by saturated steam. The laser-based system will detect the concentration of steam by shining two laser beams through a clear section of pipe and detecting the amount of light that has not been transmitted through the translucent steam. Light will be partially blocked by the microscopic water droplets that make up the saturated steam and will depend on the volumetric concentration of these droplets. Each of the lasers beams will detect precisely the same fluctuations as the inhomogeneous steam flows first past one laser beam and then the other. By identifying identical concentration fluctuations in the steam, the laser system will be able to measure the time the steam is transported from one laser to the other. From this information, the laser steam flow meter will determine the mass flow rate for saturated steam to within ±0.1%.

Fluctuations within the flowing steam will be generated through a variety of different mechanisms, including through turbulence effects from the high Reynolds number flow of the steam, imperfections in the pipe geometry and inner surface roughness, and from inhomogeneous fluctuations inherent from the act of vaporizing water. These will contribute to a variety of density fluctuation patterns along the line of the steam pipe that can be exploited for characterizing the steam mass flow rate.

Basis for Measuring Mass Flow

The net rate of mass flow through a cross sectional control surface of area A through a pipe is given by:

$$\dot{m}=c*v*A$$

Where $\dot{m}$ is mass flow, c is concentration, v is velocity of the steam, and A is the area of the cross section of the pipe carrying steam.

The velocity of the steam is measured as it passes a first light detector and a second light detector spaced along the longitudinal axis of the pipe.

The concentration is related to the absorbance as given by the Beer-Lambert Law and is a simple linear relationship.

$$Absorbance=a*b*c$$

c is concentration a is a material coefficient, b is the light path length.

Figure 1:
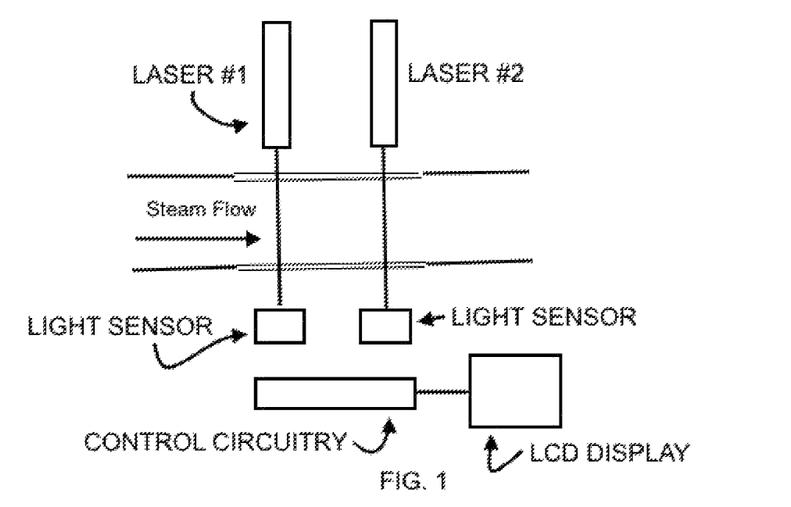
FIG. 1 is a simplified view of the apparatus used to measure mass flow.

FIG. 1 illustrates a simplified transmission of light measured by light detectors. Based on this formula, an estimate of the concentration can be determined by measuring the amount of laser light that is transmitted through the steam where the parameters a and b are known.

Mass Flow Measurement

First Method and System

Turning to FIG. 1 illustrates a steam conduit with a first and second laser beam from two laser emitters. Optionally single laser with a beam splitter could serve as a source of two laser beams. Opposing the source of laser beams is a first and a second light detector. The light detectors are spaced at a predetermined distance along the longitudinal axis of the conduit. FIG. 1 shows the source of coherent light and the corresponding light detector are normal to the longitudinal axis of the conduit. This is not required. However, it is necessary to know the distance of the light path as will be explained.

The light detectors are connected to a control circuit. The control circuit is also connected to the sources of coherent light (not shown). The light detectors are synchronized in time.

Figure 2:
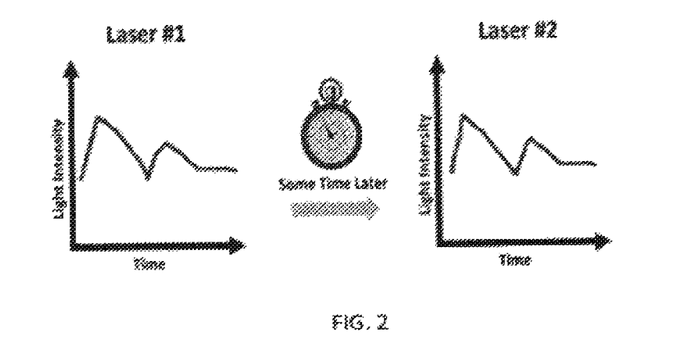
FIG. 2 is an illustration of light detection at a first and second light detector.

FIG. 2 shows that a pattern is received at the first light detector labeled #1 and then at a later time at the second light detector. This shows that the variations in the density of the water droplets in steam travel through the conduit and can be detected to record the change in concentration with time.

Figure 3:
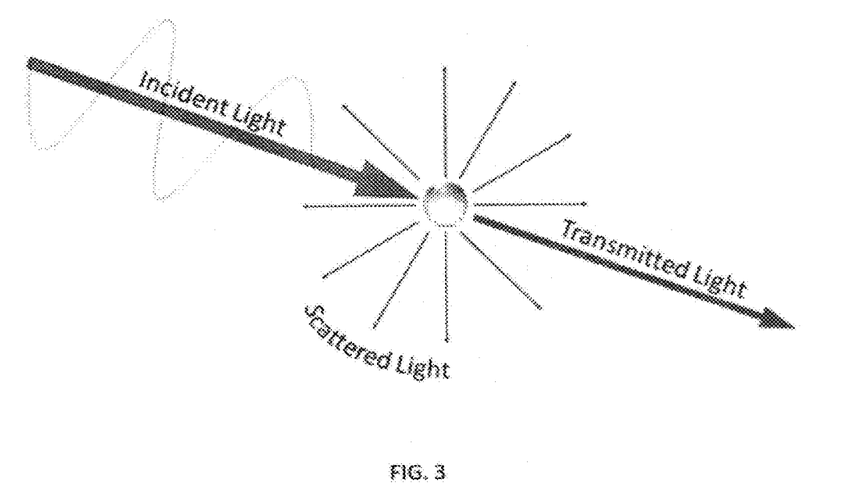
FIG. 3 is a simplified illustration of light interacting with a droplet

FIG. 3 illustrates the transmission of incident light as it encounters droplets. A portion of the light is scattered and a portion is transmitted. The light is scattered in multiple directions. The method takes advantage of cosine similarity to identify patterns in light transmission.

Figure 4:
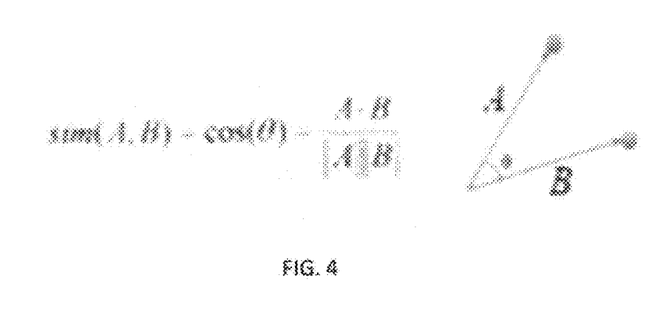
FIG. 4 is an illustration of cosine similarity.

FIG. 4 illustrates the relationship between angle θ and rays A and B.

Figure 6:
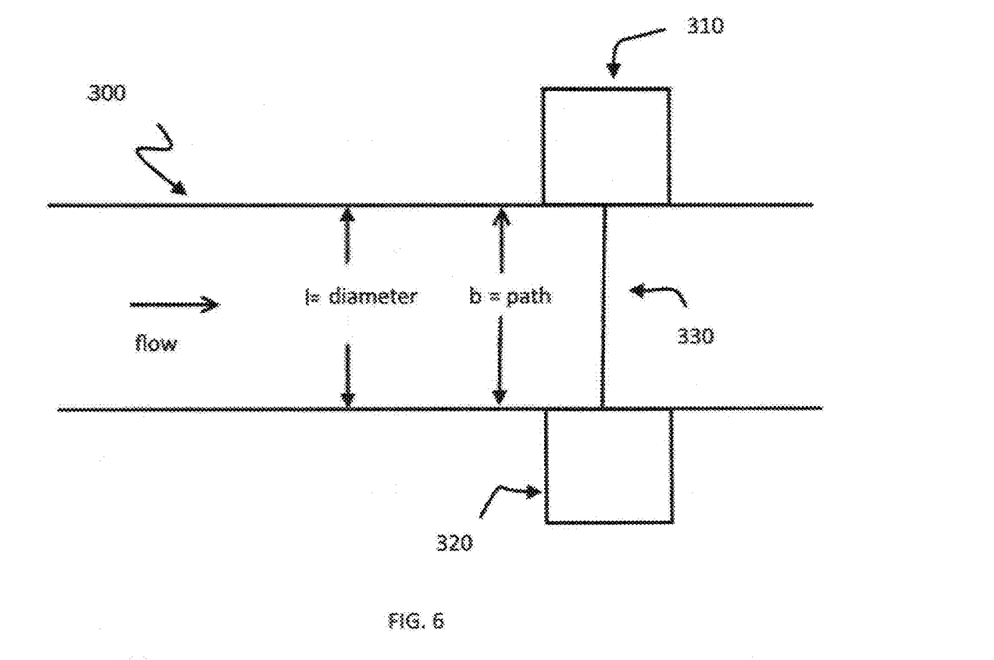
FIG. 6 is a partial plan view of a steam conduit, laser and detector.

A first method an arrangement of coherent light and detectors. FIG. 6 shows a partial plan view of the conduit 300 with a source of coherent light 310 a detector 320 corresponding to the source of coherent light 310 and a beam of coherent light 330. This is illustrative and does not show the second detector. The interior diameter l and the light path b are in this case equal, however, the light path can be any predetermined length.

Figure 8:
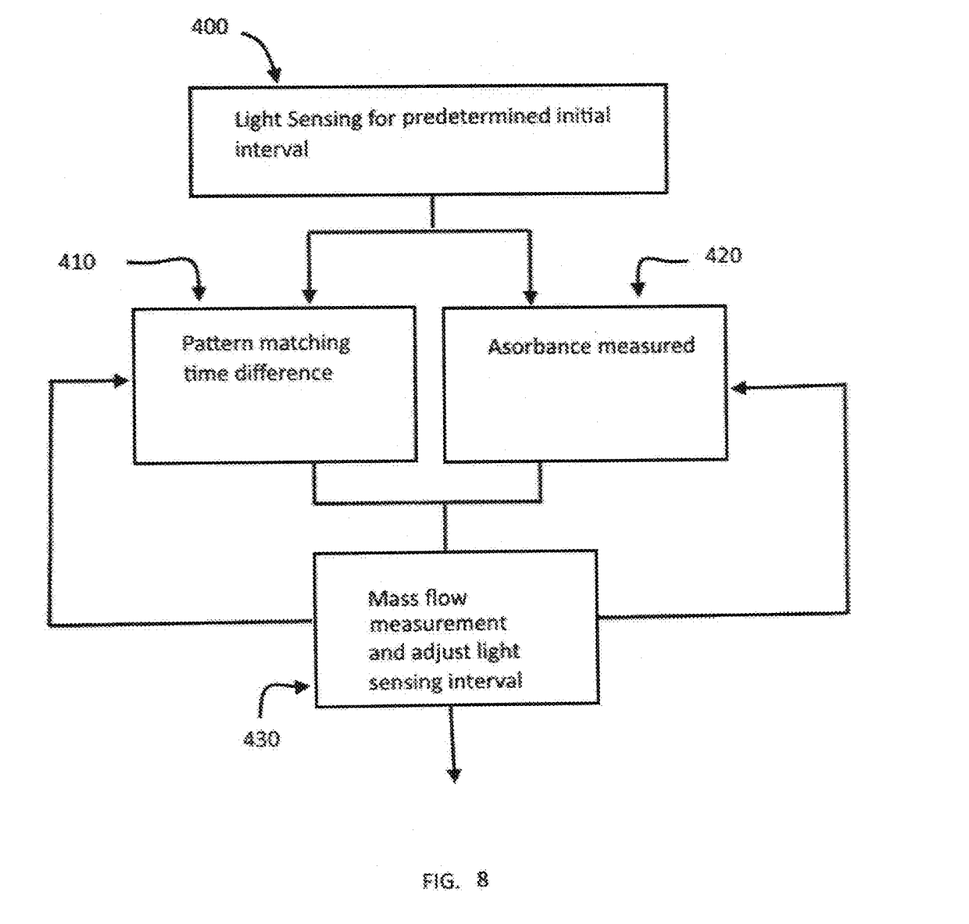
FIG. 8 is a flow chart of a first method of measurement.

FIG. 8 is a flow chart of the first method. The light detectors. The method makes two measurements generally simultaneously during a detection interval, absorbance 120 and pattern detection 110.

Figure 5:
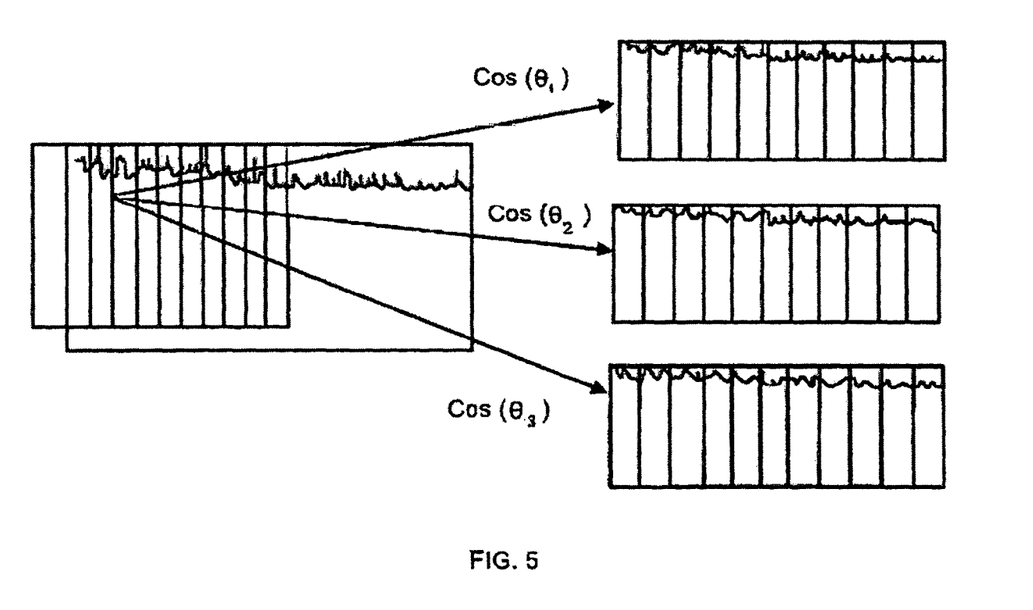
FIG. 5. Is an illustration of pattern matching.

The method records the light detection for a predetermined period 100, $t_m$. The second light detector records for an interval of $t_m+k$, where k is a predetermined number of seconds to allow for capture of the pattern. A graphic representation is show in FIG. 5 where the first detector labeled #1 records a pattern. The second light detector labeled #2 is time synchronized with the first detector and records the transmitted light and the patterns of variability in the steam flow. By using cosine similarity, the pattern can be matched as it travels past the second detector. The later arrival of the same pattern at the second detector allow a measurement of the difference in time Δt. The linear predetermined distance between the first light detector and the second light detector is Δx. Velocity is then measured as Δx/Δt.

In the same interval, absorption is measured, preferably at the first light detector. As previously stated, once the absorbance and light path are measured and knowing the coefficient a for the material (in this case steam), it is possible to measure the concentration. As given by the equation:

$$\bar{c} = \frac{\int \frac{\text{Absorbance}}{ab} dt}{t_m}$$

Where $\bar{c}$ is the average concentration a is the coefficient previously mentioned, b is the light path and $t_m$ is the predetermined interval of light detection.

The mass flow can then be measured according to the previously stated relationship $\dot{m}=c*v*A$. FIG. 8, 130.

Preferably after the initial measurement, the time to measure and optionally display the measurement on optional device, preferably an LCD screen is $t_l$. The next step of the process is then triggered. The first light detector records for the predetermined interval and the second light detector is triggered for a period of $$t_m + \frac{j*x}{v_{previous}}.$$

This adjusts the interval 130 for the second light detector to account for processing time where j is predetermined constant, x is the distance between light detectors and $v_{previous}$ is the previously measured velocity. The process continues until completed.

Second Method and System

A second method uses the same arrangement of coherent light and detectors as the first method as shown in FIG. 1.

Figure 7:
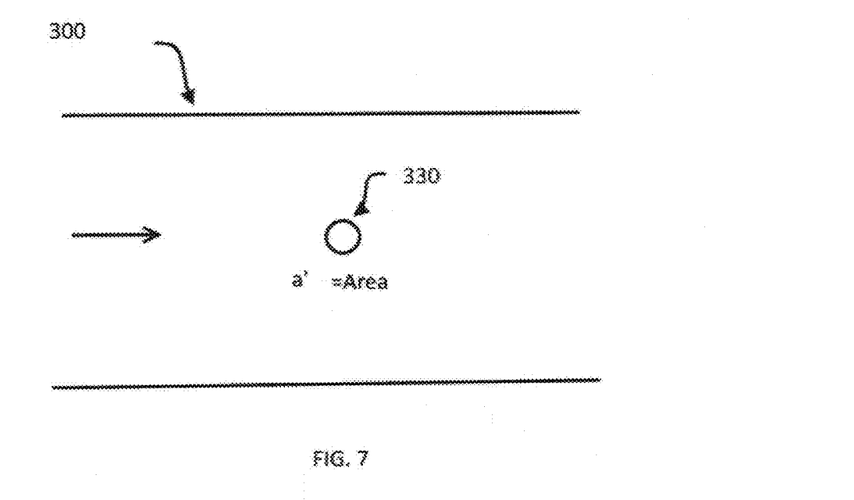
FIG. 7 is a partial plan view of a steam conduit interior.

FIG. 7 shows a partial plan view interior to the conduit 300 rotated 90 degrees with the light detector 320 and the source of coherent light 310 not shown. The beam of coherent light 330 is shown. The area of the beam of light is equal to a'.

Figure 9:
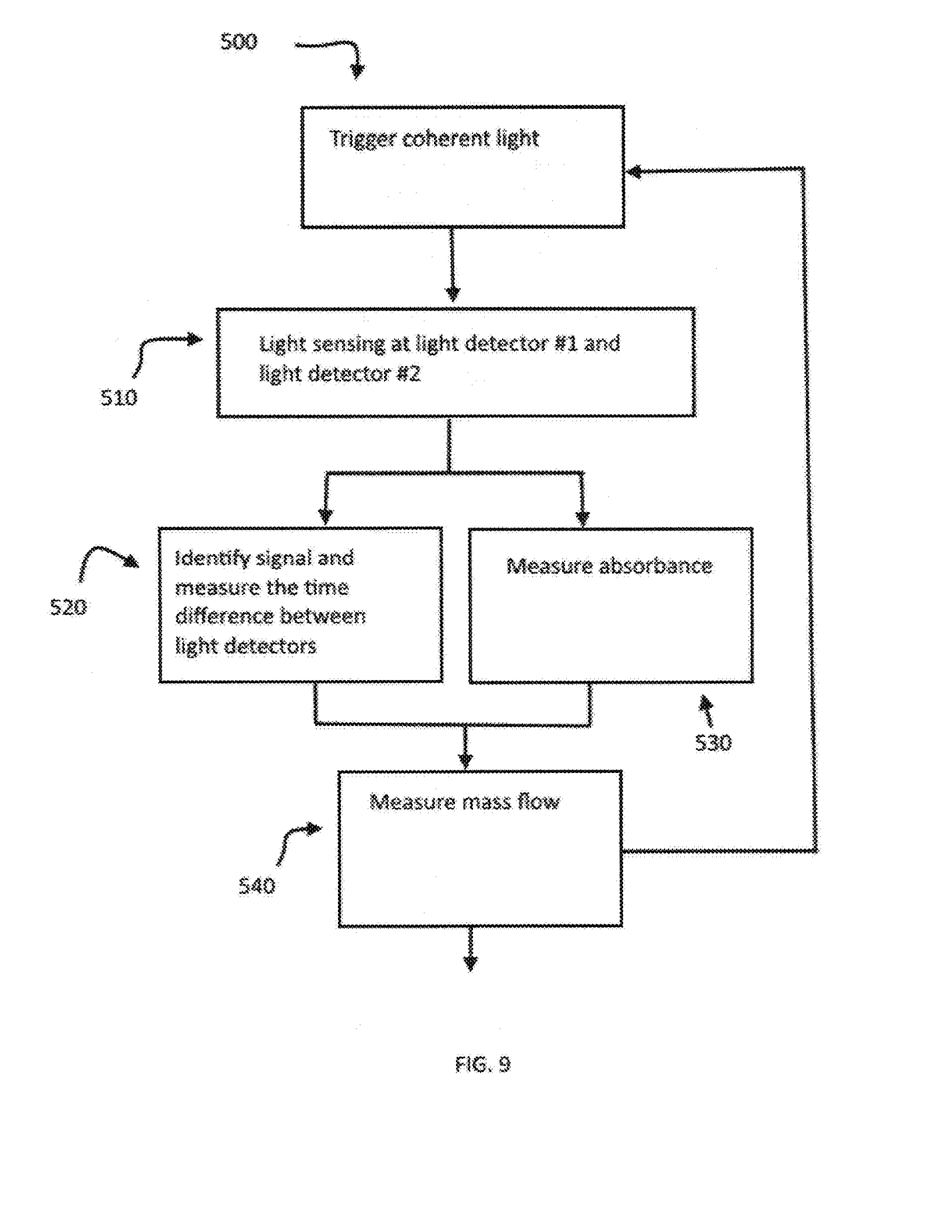
FIG. 9 is a flow chart of a second method of measurement.

The second method as shown in the flow chart in FIG. 9. The coherent light is triggered 500 and the detectors sense the coherent light 510. The first begins sensing for and interval of $t_m$ and second light detector as previously described senses the coherent light for a longer interval.

The second detector measures both the absorbance 530 and the signal that was previously received by the first detector 520.

The area of the coherent light 330 in FIG. 7 and the light path distance of the coherent beam of light 330 are known as well the absorptivity, coefficient, the distance between the detectors x and the time difference in receiving the signal Δt. The mass flow is given by:

$$\dot{m} = \frac{\frac{\text{Absorbance}}{ab}*l*a'}{\Delta t}*Z$$

The parameter Z is a compensation factor that accounts for the fact that the laser beam encompasses a smaller area than the volume of the pipe. The mass flow is measured 540 and preferably reported on a device, preferably such as an LCD screen. Then, the lasers are triggered 500 and the process is repeated until conclusion.

Although specific advantages have been enumerated above, various embodiments may include some, none, or all of the enumerated advantages. Other technical advantages may become readily apparent to one of ordinary skill in the art after review of the following figures and description.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise specifically noted, articles depicted in the drawings are not necessarily drawn to scale.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

I claim:

1. A method to measure steam quality and mass flow through a conduit having a longitudinal axis and a predetermined cross sectional area comprising:
   (a) Passing a first coherent beam of light from a first laser and a second coherent beam of light from a second laser through the conduit;
   (b) Detecting light said first beam of coherent light with a corresponding first light detector disposed generally transverse a longitudinal axis of the conduit from said first laser having a light path distance and a corresponding second light detector spaced apart along the longitudinal axis of the conduit from said second laser having a light path;
   (c) Measuring light absorbance between said first laser and said first light detector as the difference between the first laser power and the received of said first light detector;
   (d) Matching a pattern by cosine similarity between the light detected by said first and second light detector;
   (e) Measuring the difference in time between the reception of the pattern detected by the first and second light detector; and
   (f) Calculate the average concentration according to the Beer Lambert Law, velocity by said difference in time divided by said predetermined difference distance between said first laser and said second laser, and mass flow determined by the product of said concentration, said cross sectional area and said velocity of the steam.

2. A method according to claim 1 wherein in step (b) includes time synchronizing the first and second light detector.

3. A method according to claim 1 wherein in step (b) disposing the first and a second light detector along the conduit by a predetermined distance as measured along the longitudinal axis of the conduit.

4. A method according to claim 1 wherein in step (b) includes the first light detector operating for a first predetermined time interval and the second light detector operating for a second predetermined interval, said second predetermined time interval is greater than said first predetermined time interval.

5. A method according to claim 1 wherein said step (b) includes recording the detection of light from said first and said second light detectors.

6. A method according to claim 1 wherein said step (f) includes reporting the mass flow.

7. A method according to claim 1 wherein an additional step:
   (g) triggering the first coherent light emitter causing the first light detector to detect light for a third predetermined interval and the second light detector to detect light for a fourth predetermined interval and repeating steps (b)-(f) until complete.

8. A method according to claim 1 having an additional step (e) triggering the first coherent light emitter causing the first light detector to detect light for a third predetermined interval that is the first predetermined interval plus k*x/Vprevious, where k is a predetermined constant, x is the distance between the first and second light detectors and Vprevious is the velocity calculated in step (d).

9. A method to measure steam quality and mass flow through a conduit having a longitudinal axis and predetermined cross sectional area comprising:
   (a) Detecting light from a first coherent light emitter and second coherent light emitter spaced along the longitudinal axis by a corresponding first light detector and second light detectors disposed transverse to the longitudinal axis of the conduit, having spaced a predetermined distance with a measured light path length for each of the first coherent light emitter and first light detector and the second light coherent light emitter and second light detector;
   (b) Determining that the signal detected by the first detector is received by the second detector;
   (c) measuring the difference in time between the receipt of the said signal by the first detector and the receipt of the signal by the second detector;
   (d) measuring the absorbance of light through the conduit from the second coherent light emitter and the second light detector; and
   (e) calculating the velocity by dividing the predetermined distance of the spaced first and second light detectors by said difference in time, the average concentration applying the Beer Lambert Law of the flow and the mass flow determined by the product of the concentration, cross sectional area, and the velocity of the steam.

10. A claim according to claim 9 wherein the first and second light detectors are time synchronized.

11. A method according to claim 9 wherein said detecting step includes detection by the first and second light detectors for a first predetermined interval.

12. A method according to claim 9 wherein said detecting step has an additional step of recording the detection light from the first and second light detectors.

13. A method according to claim 9 wherein an additional step (f) triggering the first and second light emitters and repeating steps (a)-(e) until complete.

14. A system for measuring the average concentration velocity and mass flow of stem in a conduit comprising:
   a. At least one laser source for a first and a second coherent light beam arranged to pass through said conduit, said beams spaced a predetermined distance along the longitudinal axis of the conduit, at least one of said coherent light beams, said conduit having a predetermined cross sectional area;
   b. A first light detector corresponding to said first laser on the longitudinal axis of the conduit and a second light detector to corresponding to said second laser spaced along the longitudinal axis of the conduit spaced at a predetermined distance from said first light detector and receiving said first and said second coherent light beams, said first light detector operating for a first predetermined time interval and second light detector operating for second predetermined time interval;
   c. A light path of each of said coherent light beams each having a predetermined distance;
   d. At least one of said light detectors configured to measure the light absorbance of said at least one coherent light beam through the conduit;
   e. pattern matching circuit to compare by cosine similarity the light detected by said first and said second light detectors to measure the difference in time between the arrival of a pattern received by the first and second light detectors;
   f. calculating the velocity by dividing the predetermined distance of the spaced first and second light detectors by said difference in time, the average concentration applying the Beer Lambert Law of the flow and the mass flow determined by the product of the concentration, cross sectional area, and the velocity of the steam;

g. reporting the said measurements; and h. adjusting the second predetermined time interval by accounting for processing time and repeating the process until completion.

15. A system for measuring the velocity and mass flow of steam in a conduit comprising:

a. At least on source for a first and a second coherent light beam arranged to pass through said conduit, said beams spaced a predetermined distance along the longitudinal axis of the conduit, at least one of said coherent light beams having a predetermined area;

b. A first and a second light detector to corresponding to and receiving said first and said second coherent light beams, said first light detector operating for a first predetermined time interval and second light detector operating for second predetermined time interval;

c. A light path of said coherent light beams having a predetermined distance;

d. At least one of said light detectors configured to measure the absorbance of said at least one coherent light beam;

e. said first and second light detectors configured to measure the difference in time between the arrival of a signal received by the first and second light detectors;

f. Reporting the steam mass flow from said absorbance, said time difference, said light path distance, said predetermined spacing of said first and second light detectors, said light beam area and said interior diameter of said conduit;

g. Triggering said coherent light sources and said light detectors and repeating the process until conclusion.

* * * * *